United States Patent
Overweg et al.

(10) Patent No.: US 10,433,729 B2
(45) Date of Patent: Oct. 8, 2019

(54) RF SHIELDED EXAM ROOM OF A MAGNETIC RESONANCE IMAGING SYSTEM

(71) Applicant: KONINKLIJKE PHILIPS N.V., Eindhoven (NL)

(72) Inventors: Johannes Adrianus Overweg, Eindhoven (NL); Falk Uhlemann, Eindhoven (NL)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 918 days.

(21) Appl. No.: 14/895,238

(22) PCT Filed: May 23, 2014

(86) PCT No.: PCT/EP2014/060719
§ 371 (c)(1),
(2) Date: Dec. 2, 2015

(87) PCT Pub. No.: WO2014/195158
PCT Pub. Date: Dec. 11, 2014

(65) Prior Publication Data
US 2016/0106317 A1   Apr. 21, 2016

(30) Foreign Application Priority Data

Jun. 6, 2013 (EP) .................................... 13170802

(51) Int. Cl.
*A61B 5/00* (2006.01)
*A61B 5/055* (2006.01)
(Continued)

(52) U.S. Cl.
CPC ............ *A61B 5/0046* (2013.01); *A61B 5/055* (2013.01); *G01R 33/288* (2013.01);
(Continued)

(58) Field of Classification Search
USPC .......................... 324/300–322; 600/407–435; 382/128–131
See application file for complete search history.

(56) References Cited

U.S. PATENT DOCUMENTS 4,613,820 A * 9/1986 Edelstein ............... G01D 11/24
                                                    324/300
4,646,046 A * 2/1987 Vavrek ................... G12B 17/02
                                                    174/384
(Continued)

FOREIGN PATENT DOCUMENTS

EP           2359905 A1    8/2011
JP           63145642 A    6/1988
(Continued)

*Primary Examiner* — Melissa J Koval
*Assistant Examiner* — Tiffany A Fetzner
(74) *Attorney, Agent, or Firm* — Sherry Austin

(57) ABSTRACT

An exam room shielding (10) for electromagnetically shielding a magnetic resonance imaging system (2) includes: a ceiling, a floor, side walls (11) interconnecting the ceiling and the floor, and a tubular shielding device (12), which is arranged to surround an examination tube (3) of the magnetic resonance imaging system (2). Both longitudinal ends (13) of the tubular shielding device (12) are circumferentially connected to openings (14) of the side walls (11) which form the outline of an U-shaped room (15) with the longitudinal ends (13) of the tubular shielding device (12) interconnecting the lateral flanks (16) of the U-shaped room (15). A magnetic resonance imaging system (2) includes an exam room (1), with the above exam room shielding (10). An additional treatment or diagnosis device (7) can be located at an outer circumference of the tubular shielding device (12). This separates the space inside the exam room into a compartment free of RF noise, i.e. the space surrounded by the exam room shielding, for MR scanning, and a compartment outside the shielding, in which an operator can move (Continued)

for operating the MR imaging system and/or preparing a person for a MR scan.

18 Claims, 3 Drawing Sheets

(51) Int. Cl.
    *G21F 7/00* (2006.01)
    *G01R 33/28* (2006.01)
    *G01R 33/385* (2006.01)
    *G01R 33/422* (2006.01)
    *G01R 33/48* (2006.01)

(52) U.S. Cl.
    CPC ......... *G01R 33/385* (2013.01); *G01R 33/422* (2013.01); *G21F 7/00* (2013.01); *G01R 33/4808* (2013.01)

(56) References Cited

U.S. PATENT DOCUMENTS

| | | | | |
|---|---|---|---|---|
| 4,651,099 | A * | 3/1987 | Vinegar | G01R 33/28 174/384 |
| RE33,505 | E * | 12/1990 | Vinegar | G01R 33/28 324/320 |
| 6,590,391 | B1 * | 7/2003 | Shudo | G01R 33/3852 324/318 |
| 7,529,575 | B2 * | 5/2009 | Rezzonico | A61B 5/0555 324/318 |
| 9,138,145 | B2 * | 9/2015 | Klimenko | A61B 5/055 |
| 9,817,089 | B2 * | 11/2017 | Biber | G01R 33/30 |
| 2002/0057088 | A1 * | 5/2002 | Carrozzi | A61B 5/0555 324/318 |
| 2005/0049491 | A1 * | 3/2005 | Rezzonico | A61B 5/0555 600/436 |
| 2005/0073308 | A1 * | 4/2005 | Havens | G01R 33/422 324/318 |
| 2009/0124887 | A1 | 5/2009 | Roell | |
| 2011/0260729 | A1 | 10/2011 | Carlone | |
| 2015/0141799 | A1 * | 5/2015 | Rapoport | A61B 5/0555 600/410 |
| 2015/0253401 | A1 * | 9/2015 | Rapoport | A61B 5/055 324/318 |
| 2016/0106317 | A1 * | 4/2016 | Overweg | G01R 33/422 600/411 |
| 2019/0133538 | A1 * | 5/2019 | Bourne | A61B 5/7445 |
| 2019/0137583 | A1 * | 5/2019 | Mikeska | G01R 33/422 |

FOREIGN PATENT DOCUMENTS

| | | |
|---|---|---|
| JP | 02203840 A | 8/1990 |
| JP | 08154912 A | 6/1996 |
| JP | 2005270422 A | 10/2005 |
| WO | 03008986 A2 | 1/2003 |

\* cited by examiner

RF SHIELDED EXAM ROOM OF A MAGNETIC RESONANCE IMAGING SYSTEM

CROSS REFERENCE TO RELATED APPLICATIONS

This application is a U.S. national phase application of International Application No. PCT/EP2014/060719, filed on May 23, 2014, which claims the benefit of EP Application Serial No. 13170802.6 field on Jun. 6, 2013 and is incorporated herein by reference.

FIELD OF THE INVENTION

The invention relates to the field of magnetic resonance (MR) imaging, in particular in conjunction with the use of diagnostic or treatment devices like linear accelerator devices or others.

BACKGROUND OF THE INVENTION

Electromagnetic shielding of a magnetic resonance (MR) imaging system is an important requirement for reliable operation thereof and a basis for generation of high quality diagnostic images. Such an electromagnetic shielding is provided as a Faraday cage to enable a shielding of RF irradiation. Accordingly, components of the MR imaging system involved in the generation or measurement of electromagnetic fields as well as components for analogous signal transmission require a shielding. In particular, the main magnet with gradient and RF coils, which surround an examination space, are located within a shielding, which is typically provided as an exam room shielding.

Electromagnetic shielding becomes more complicated when an MR imaging system is used together with at least one other device, which has to be located in vicinity of the MR imaging system. This refers to a combination of the MR imaging system with other diagnostic or treatment devices, for example the combination of a linear accelerator (linac) device with an MR imaging system. Such a combination enables e.g. the generation of diagnostic images with the MR imaging system during the treatment with the linac device for controlling the operation of the linac device and the efficiency of the treatment using the linac device.

The U.S. Pat. No. 4,613,820 discloses a radio-frequency shielded room for a nuclear magnetic resonance imaging system. An electrically conductive shield wall enclosing a volume is provided adjacent to one end of the magnet bore.

For the MR imaging system, the linac device is an important source of electromagnetic interferences and vice versa, since both devices generate RF irradiation during operation. Another example for such a diagnostic or treatment device is a hyperpolarisation device. Accordingly, it is required to adapt the electromagnetic shielding of the MR imaging system to achieve a reliable RF-shielding thereof under consideration of spatial requirements as well as structural requirements for locating and supporting the other device as well as the MR imaging system. In particular, a reliable shielding of the MR imaging system from electromagnetic interferences generated by the other device is required. Furthermore, also the other device may require shielding from the electromagnetic irradiation generated by the MR imaging system.

An improved electromagnetic shielding comprises a tubular shielding device, which is arranged to surround an examination tube of the magnetic resonance imaging system. Usually, also gradient coils of the MR imaging system, e.g. as a gradient coil assembly, are positioned within the tubular shielding device. The shielding extends from the longitudinal ends of the tubular shielding device to enable access for staff and patients. This results in the exam room shielding being separated by the tubular shielding device into two spaces, one at each longitudinal end of the tubular shielding device. Accordingly, access to the examination tube is rather complicated, especially when access to the examination tube is required alternately from the opposite ends thereof. The access refers to access for maintenance purposes as well as during normal operation. For example, a patient can be placed into the examination tube from one of its ends, and the provisioning of additional coils or supplementary devices like contrast agent supply devices or oxygen supply devices may require access from the opposite end of the examination tube. This is rather uncomfortable for patients and staff.

Additional aspects when using MR imaging systems together with other devices are system installation, maintenance, and repair, which have to be considered in the design of the exam room shielding. The separation of the space by the exam room shielding increases the effort for installation, maintenance, and repair.

SUMMARY OF THE INVENTION

It is an object of the invention to provide an exam room shielding, a magnetic resonance imaging system comprising an exam room having a shielding and a system comprising a magnetic resonance imaging system and an additional treatment or diagnostic device located at an outer circumference of the tubular shielding device, which have good shielding capabilities and offer good ergonomics for operation, for maintaining the magnetic resonance imaging system, and for preparing and caring about patients located within an examination space of the magnetic resonance imaging system.

This object is achieved by an exam room shielding for electromagnetically shielding a magnetic resonance imaging system, the exam room shielding comprising a ceiling, a floor, side walls interconnecting the ceiling and the floor, and a tubular shielding device, which is arranged to surround an examination tube of the magnetic resonance imaging system, wherein both longitudinal ends of the tubular shielding device are circumferentially connected to openings of the side walls, and the side walls of the shielding form the outline of an U-shaped room with the longitudinal ends of the tubular shielding device interconnecting the lateral flanks of the U-shaped room.

This object is also achieved by a magnetic resonance imaging system comprising an exam room, wherein the exam room has an exam room shielding as specified above.

Furthermore, this object is achieved by a system comprising the above magnetic resonance imaging system and an additional treatment or diagnostic device located at an outer circumference of the tubular shielding device.

The proposed exam room shielding separates a space inside the exam room into two compartments, which are separated in terms of RF irradiation, in particular RF noise. One compartment, i.e. the first compartment, is the compartment within the exam room shielding containing the examination tube, where the electromagnetic fields are applied for performing a magnetic resonance scan. The other compartment, i.e. the second compartment, comprises a space within the exam room, but outside the exam room shielding, including a space outside of the tubular shielding device. This space outside of the tubular shielding device encompasses also the space surrounding the examination tube, where the other devices are located, and optional neighboring rooms, where operators and/or service personnel can move for operating the MR imaging system and/or the other devices. Furthermore, also a person can be prepared for being subject of a MR scan in such a neighboring room. The first compartment of the exam room is not further separated by the exam room shielding. This topology allows integration of different devices which would, without such an electromagnetic exam room shielding, cause mutual electric interference due to spatial proximity.

The interior of the examination tube, which is open at both longitudinal ends, is also shielded, so that the MR imaging system can be operated without additional limitations. With the shielding of the examination tube by the tubular shielding device, additional devices can be located in vicinity of the examination tube. The other devices in general refer to diagnostic or treatment devices, which are operated together with the MR imaging system, for example a linear accelerator (linac) device or a hyperpolarisation device. Nevertheless, any kind of device that generates electromagnetic irradiation in vicinity of the examination space can be considered as other device.

This design of the exam room shielding enables the reuse of current components of MR imaging systems. Furthermore, a combination with the other device can be easily implemented without modifications of the other device. Access to the other device can be easily realized without entering the shielding through the resulting opening between the lateral flanks of the shielding. Also, an additional shielding of the other device can be omitted, since the shielding is already achieved by the exam room shielding.

According to a preferred embodiment the tubular shielding device is provided integrally with a main magnet of the magnetic resonance imaging system. When the main magnet is provided with an electrically conductive material, this material can be used for shielding purposes to provide an RF shielding. The tubular shielding device is preferably provided as the main magnet, i.e. the main magnet alone serves as tubular shielding device. In another embodiment, the tubular shielding device comprises at least one tube section independent from the main magnet and connected thereto, so that the tube section and the main magnet form two sections of the tubular shielding device.

According to a preferred embodiment the main magnet is a superconducting magnet, which comprises an outer vacuum container made of an electromagnetically shielding material, and the tubular shielding device is provided integrally with the outer vacuum container. Preferably, the superconducting magnet has a cylindrical shape having any suitable cross-section including a circular or oval cross-section. The outer vacuum container of the main magnet is usually a thick-walled stainless-steel or aluminum structure which can perform the function of the tubular shielding device for providing an electromagnetic shielding. Accordingly, the lateral flanks of the exam room shielding are electrically connected thereto. Preferably, the electrical connection between the exam room shielding and the outer vacuum container extends over the entire circumference of the magnet. The connection can be provided close to an inner radius of end-flanges of the main magnet, close to an outer radius of these flanges, anywhere in between at these flanges, or at the cylindrical outer surface of the vacuum container.

According to a preferred embodiment the U-shaped room is provided with operational spaces, which are located in front of the longitudinal ends of the tubular shielding device. The operational spaces are suitable for preparing a patient and caring about a patient during the MR scan and/or a treatment or diagnosis performed by the other device. The space is suitable for driving an examination table, where the patient lays during the imaging and/or treatment, out of the examination tube, and to allow an operator to move around the examination table. When the examination table is movable out of the examination tube towards one of its longitudinal ends, the operational spaces on the longitudinal ends can be provided differently, i.e. with different size and shape. With the two operational spaces, the patient can be prepared at the table at one end of the examination tube, and access is possible from any side during operation of the MR imaging system, e.g. for provisioning additional coils for MR imaging or supplementary devices like contrast agent supply devices or oxygen supply devices.

According to a preferred embodiment the U-shaped room is provided with a walkway between the operational spaces. The walkway can have any shape and width suitable for a person to pass between the operational spaces. The walkway is not limited to shape and width, where only a person can pass, but can have any bigger width and different shape. The walkway enables quick access to the examination tube, so that a single operator can perform all necessary steps for patient preparation and assistance.

According to a preferred embodiment the exam room shielding comprises a cable duct, which is arranged within an inner space of the exam room shielding. The cable duct facilitates cabling of the MR imaging system. Preferably, the cable duct extends to a position where at least one cable penetrates the exam room shielding. Hence, a cable can penetrate the RF shielding at one location and, once inside the exam room shielding, be guided using the cable duct to any place within the exam room shielding. Further preferred, the cable duct is arranged to interconnect the longitudinal ends of the tubular shielding device. Accordingly, a cable can easily be routed to both ends of the examination tube.

According to a preferred embodiment the cable duct is arranged along at least one side wall of the shielding. Accordingly, the cable duct does not interfere with other components within the exam room shielding and without limiting a movement of the operator within the exam room shielding. Preferably, a connection between the longitudinal ends of the tubular shielding device is provided along at least one side wall.

According to a preferred embodiment the exam room shielding comprises a filter box for through connection of at least one electric cable. The filter box enables the through connection of cables between the interior and the exterior of the exam room shielding without any gap of the shielding. Size and location of the filter box can be chosen as required. Preferably, only one single filter box is provided for the through connection of all cables. Multiple filter boxes would result in more than a single ground point of the RF shielding; which is to be avoided since this can result in deterioration of the shielding performance.

BRIEF DESCRIPTION OF THE DRAWINGS

These and other aspects of the invention will be apparent from and elucidated with reference to the embodiments described hereinafter. Such an embodiment does not necessarily represent the full scope of the invention, however, and reference is made therefore to the claims and herein for interpreting the scope of the invention.

In the drawings.

DETAILED DESCRIPTION OF EMBODIMENTS

Figure 1:
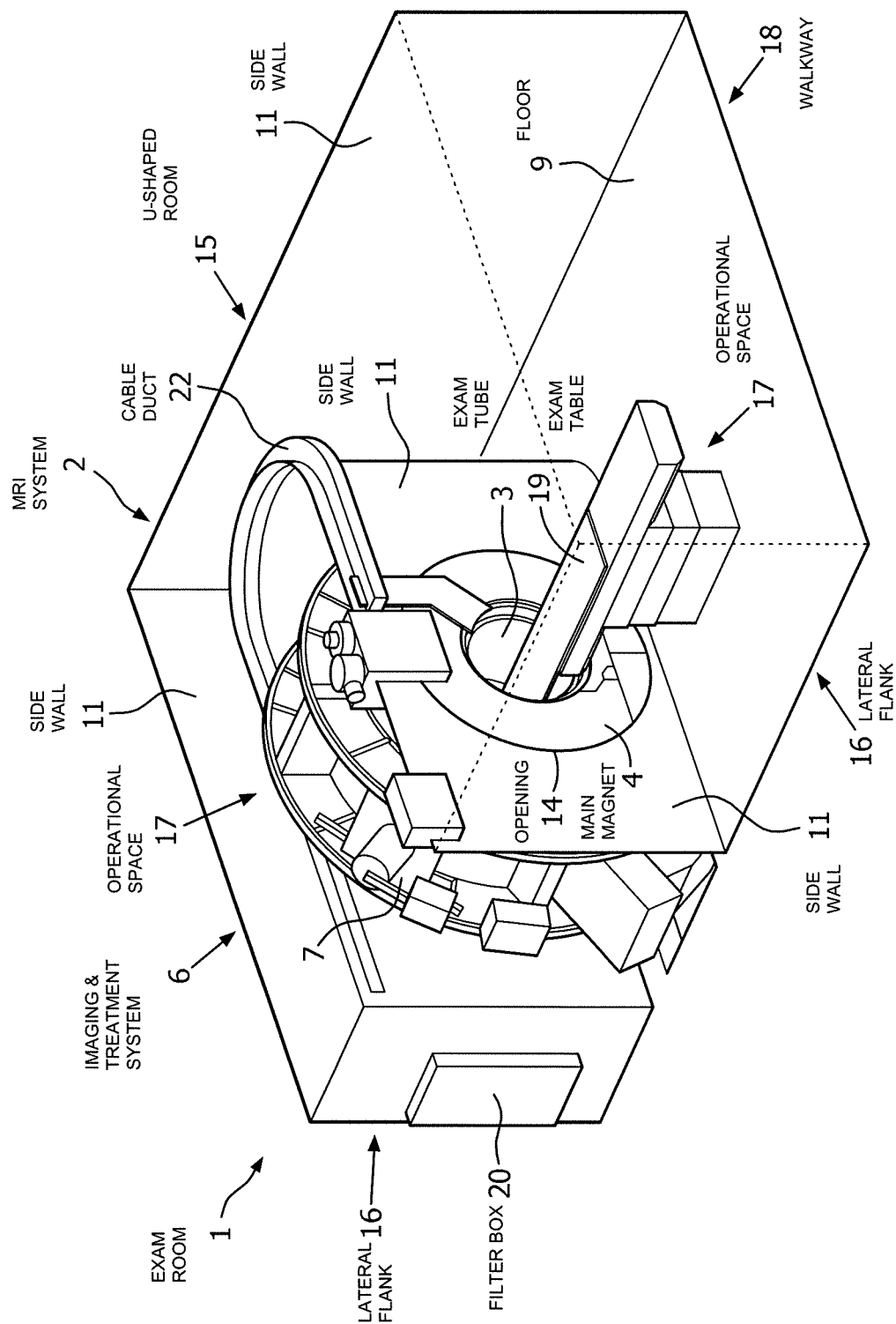
FIG. 1 shows a perspective view of an exam room of a magnetic resonance imaging system with an exam room shielding and an additional linac device according to a general setup, and FIG. 2 schematically shows a detailed top view of the general exam room of FIG. 1 according to a first embodiment, and FIG. 3 schematically shows a detailed top view of the general exam room of FIG. 1 according to a second embodiment.

FIGS. 1 shows a general setup of an exam room 1 of a magnetic resonance (MR) imaging system 2. The general setup of the MR imaging system 2 comprises an examination tube 3, a main magnet 4 and a gradient coil assembly 5, whereby the main magnet 4 and the gradient coil assembly 5 are located to surround the examination tube 3, as can be best seen in FIGS. 2 and 3.

The MR imaging system 2 is part of an imaging and treatment system 6 comprising an additional linac device 7, which is operated together with the MR imaging system 2. The linac device 7 is located at an outer circumference of the main magnet 4.

The exam room 1 has an exam room shielding 10 for electromagnetically shielding the MR imaging system 2, Accordingly, the exam room shielding 10 is made of an electrically conductive material. The exam room shielding 10 comprises a ceiling, which is not shown in the figures, a floor 9 of the exam room 1, and side walls 11 interconnecting the ceiling and the floor 9.

The side walls 11 of the exam room shielding 10 form the outline of a U-shaped room 15 with the longitudinal ends 13 of the examination tube 3 of the magnetic resonance imaging system 2 interconnecting the lateral flanks 16 of the U-shaped room 15.

The U-shaped room 15 is provided with operational spaces 17, which are located in front of the longitudinal ends 13 of the examination tube 3. The U-shaped room 15 is provided with a walkway 18 between the operational spaces 17, which is the base of the U-shaped room 15 in this embodiment. An examination table 19 is located inside the exam room shielding 10, so that a patient lying on this examination table 19, can be moved from one operational space 17 into the examination tube 3 and vice versa.

Figure 2:
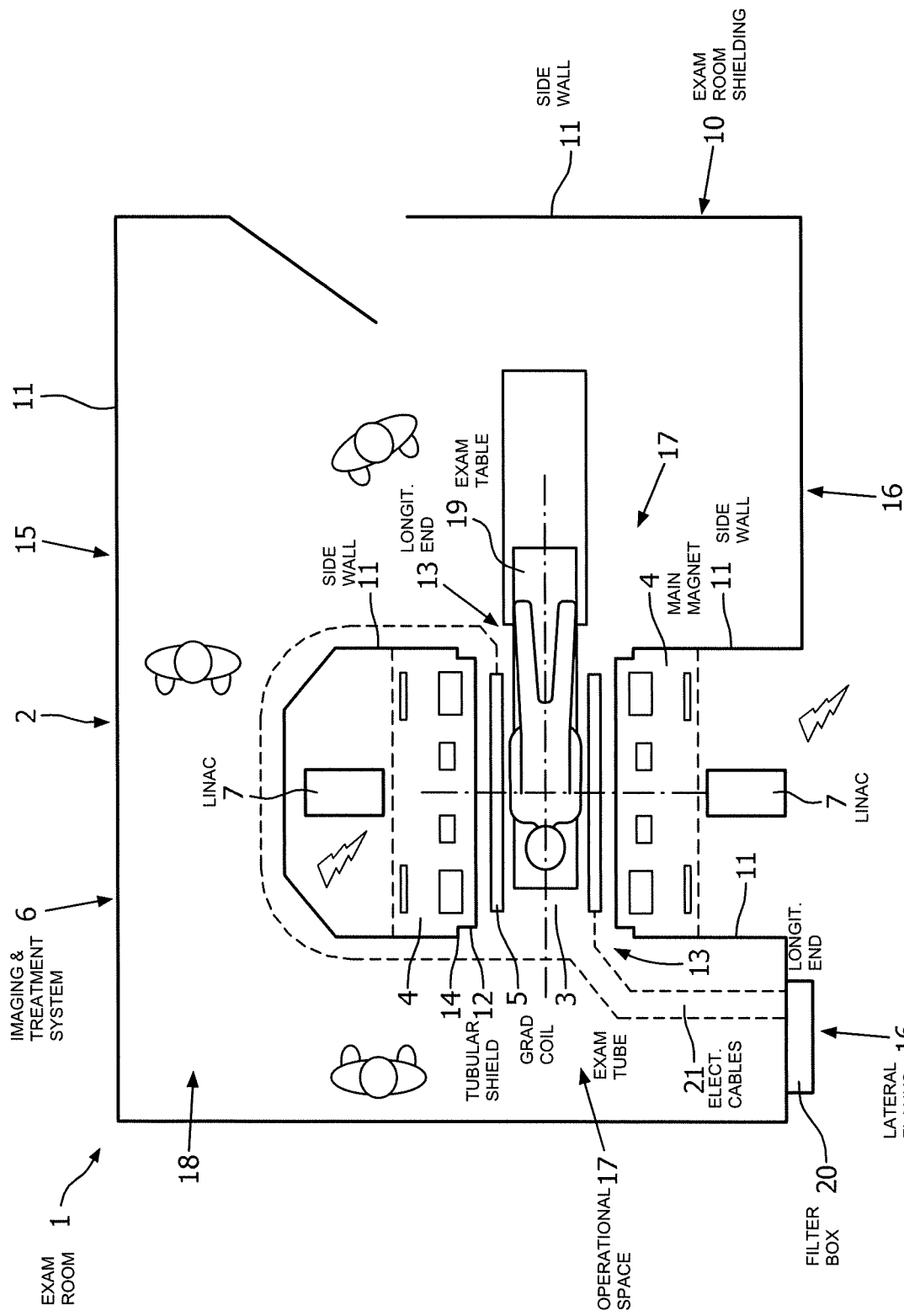
Figure 3:
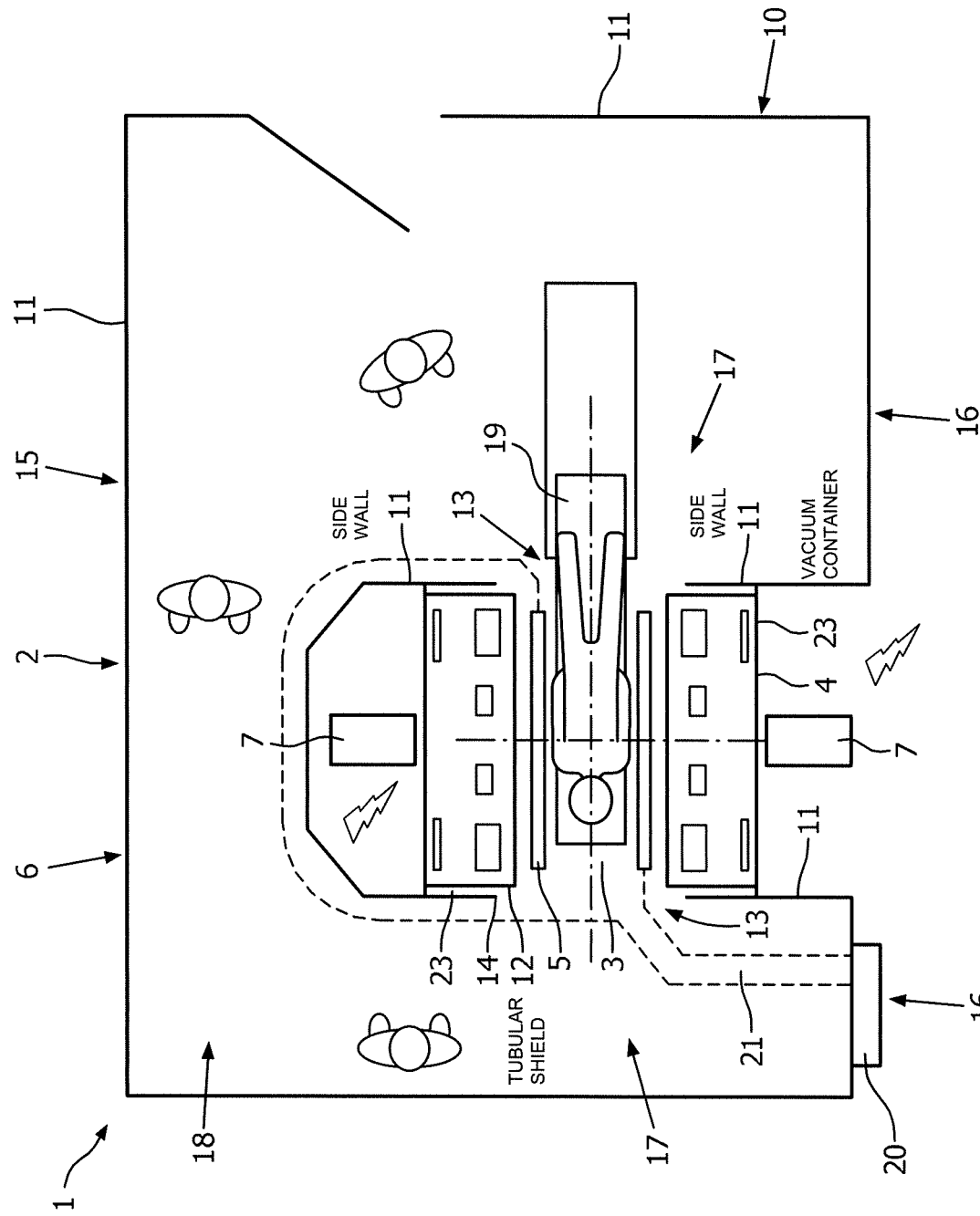

The exam room shielding 10 further comprises a filter box 20 for through connection of electric cables 21. The electric cables 21 are amongst others connected to the gradient coil assembly 5 at both longitudinal ends 13 of the examination tube 3, as schematically shown in FIGS. 2 and 3. As can be seen in FIG. 1, the exam room shielding 10 comprises a cable duct 22, which is arranged within an inner space of the exam room shielding 10 along a side wall 11 thereof. The cable duct 22 interconnects the longitudinal ends 13 of the examination tube 3.

Starting from this general setup, according to a first embodiment, which is shown in FIG. 2, the exam room shielding 10 further comprises a tubular shielding device 12, which is arranged to surround the examination tube 3 and the gradient coil assembly 5. The tubular shielding device 12 is made of an electrically conductive material as RF shield. The main magnet 4 and the linac device 7 are located at an outer circumference of the tubular shielding device 12. Both longitudinal ends 13 of the tubular shielding device 12 are circumferentially connected to openings 14 of the side walls 11 to provide an electrically conductive connection therebetween. Accordingly, a fully shielded compartment is formed within the exam room 1, where the examination tube 3 and the gradient coil assembly 5 as well as cables 21 are shielded from the main magnet 4 and the linac device 7.

Starting again from the general setup, according to a second embodiment, which is shown in FIG. 3, the exam room shielding 10 further comprises a tubular shielding device 12, which is provided integrally with the main magnet 4. The main magnet 4 is provided having an outer vacuum container 23, which is a thick-walled stainless-steel or aluminum structure. The side walls 11 of the lateral flanks 16 of the exam room shielding 10 extend over the entire circumferential flanges of the main magnet 4. The side walls 11 are electrically connected to the outer vacuum container 23 close to the outer radius of the flanges of the main magnet 4. Accordingly, a fully shielded compartment is formed within the exam room 1, where the examination tube 3 and the gradient coil assembly 5 are shielded from the main magnet 4 and the linac device 7, and the linac device 7 is shielded from the examination tube 3, the gradient coil assembly 5, and the main magnet 4

While the invention has been illustrated and described in detail in the drawings and foregoing description, such illustration and description are to be considered illustrative or exemplary and not restrictive; the invention is not limited to the disclosed embodiments. Other variations to the disclosed embodiments can be understood and effected by those skilled in the art in practicing the claimed invention, from a study of the drawings, the disclosure, and the appended claims. In the claims, the word "comprising" does not exclude other elements or steps, and the indefinite article "a" or "an" does not exclude a plurality. The mere fact that certain measures are recited in mutually different dependent claims does not indicate that a combination of these measures cannot be used to advantage. Any reference signs in the claims should not be construed as limiting the scope.

REFERENCE SYMBOL LIST 1 exam room
2 magnetic resonance imaging system
3 examination tube
4 main magnet
5 gradient coil assembly
6 imaging and treatment system
7 linac device
9 floor
10 exam room shielding
11 side wall
12 tubular shielding device
13 longitudinal end
14 side wall opening
15 U-shaped room
16 lateral flanks
17 operational space
18 walkway
19 examination table
20 filter box
21 electric cable
22 cable duct
23 outer vacuum container

The invention claimed is:

1. An exam room shielding arranged for electromagnetically shielding a magnetic resonance imaging system, the arrangement of the exam room shielding comprising:

shielding of a ceiling of the exam room,
shielding of a floor of the exam room,
shielding side walls which interconnects the ceiling shielding of the exam room and the floor shielding of the exam room, along with a tubular shielding device, which is arranged to surround an examination tube of the magnetic resonance imaging system,
wherein both longitudinal ends of the tubular shielding device are circumferentially connected to openings of the shielded side walls, and
the side walls of the exam room shielding forming the outline of a U-shaped room, within the exam room, that extends between the floor shielding and the ceiling shielding, with the longitudinal ends of the tubular shielding device interconnecting the lateral flanks of the side wall outline that forms the U-shaped shielded room, inside the exam room configured for containing the magnetic resonance imaging system.

2. The exam room shielding according to claim 1, wherein the tubular shielding device is provided integrally with a main magnet of the magnetic resonance imaging system.

3. The exam room shielding according to claim 2, wherein the main magnet is a superconducting magnet, which comprises an outer vacuum container made of an electromagnetically shielding material, and
the tubular shielding device is provided integrally with the outer vacuum container.

4. The exam room shielding according to claim 1, wherein the exam room shielding arrangement defines operational spaces as part of the formed outline of the U-shape which is configured to receive clinicians, the operational spaces being located in front of the longitudinal ends of the tubular shielding device such that the clinicians can access a patient in the examination tube from both longitudinal ends.

5. The exam room shielding according to claim 4, wherein the exam room shielding is configured to define a walkway between the operational spaces, which receive the clinicians, such that the clinicians can walk within the arrangement of the exam room shielding between the operational spaces of the exam room.

6. The exam room shielding according to claim 1, wherein the exam room shielding further comprises a cable duct, which is arranged within an inner space of the exam room shielding.

7. The exam room shielding according to claim 6, wherein the cable duct is arranged along at least one side wall of the exam room shielding.

8. The exam room shielding according to claim 1, wherein the exam room shielding further comprises a filter box configured to provide a through connection for at least one electric cable.

9. A shielded magnetic resonance imaging system within an exam room, wherein the exam room has an exam room shielding arranged according to claim 1.

10. A shielded magnetic resonance imaging system comprising a magnetic resonance imaging system according to claim 9 and an additional treatment or diagnostic device which is located at an outer circumference of the tubular shielding device.

11. The exam room shielding according to claim 1, wherein the formed outline of the U-shaped shielded room within the exam room, extends partially around the magnetic resonance imaging system separating the magnetic resonance imaging system and operational spaces that are disposed adjacent to one another on each longitudinal end of the examination tube, with the operational spaces being configured to receive clinicians.

12. The exam room shielding according to claim 11, wherein the openings of the shielded side walls, are disposed in the outline of the U-shaped room formed by the side walls themselves.

13. The exam room shielding according to claim 12, further including a walkway disposed adjacent the U-shaped room connecting the operational spaces on either side of the U-shaped room.

14. An exam room shielding arranged for electromagnetically shielding a magnetic resonance imaging system including a patient receiving examination tube, the arrangement of the electromagnetic shielding comprising:
shielding of a ceiling of the exam room,
shielding of a floor of the exam room,
shielding within side walls which interconnects the ceiling shielding of the exam room and the floor shielding of the exam room, along with a tubular electromagnetic shielding device which is arranged to surround the examination tube of the magnetic resonance imaging system,
wherein the side walls of the electromagnetic shielding also surround the exam room and include a shielded U-shaped region extending partially around the magnetic imaging system between the magnetic resonance imaging system and operational spaces located within the exam room that are configured to receive clinicians adjacent two longitudinal ends of the examination tube of the magnetic resonance imaging system; and
wherein the two longitudinal ends of the tubular electromagnetic shielding device are circumferentially connected to a pair of openings in the U-shaped region of the side walls.

15. The exam room shielding according to claim 14, wherein the exam room shielding arrangement defines the operational spaces as part of the formed outline of the U-shape which is configured to receive clinicians in front of the longitudinal ends of the tubular shielding device such that the clinicians can access a patient in the examination tube from both longitudinal ends.

16. A shielded magnetic resonance imaging system within an exam room, wherein the exam room has an exam room shielding arranged according to claim 14.

17. A shielded magnetic resonance imaging system comprising a magnetic resonance imaging system according to claim 16 and an additional treatment or diagnostic device which is located at an outer circumference of the tubular shielding device.

18. An exam room shielding for electromagnetically shielding a magnetic resonance exam room including:
a floor configured to support a magnetic resonance imaging (MRI) system having a patient receiving exam tube extending from a first end to a second end,
side walls displaced from the MRI system that are configured to provide operational spaces adjacent the examination tube extending from the first end and extending from the second end in order for clinicians to access a patient in the examination tube, and
a ceiling;
wherein electromagnetic shielding is present in the ceiling, floor, and sidewalls, the electromagnetic shielding comprising:
side wall shielding extending between the ceiling shielding and floor shielding, the side wall shielding also extending in a U-shape partially around the MRI system and around the side walls of the exam room as well as around the operational spaces and around a walkway existing between the operational spaces, the side wall electromagnetic shielding defining an aperture at each end of the examination tube in order to allow access to a patient in the examination tube from the first and second ends by clinicians who are located with within the operational spaces, the side wall shielding also being circumferentially connected around the defined aperture with a tubular electromagnetic shielding device surrounding the examination tube.

\* \* \* \* \*